United States Patent [19]
Talonn et al.

[11] Patent Number: 5,160,326
[45] Date of Patent: Nov. 3, 1992

[54] COMBINED SYRINGE AND NEEDLE SHIELD

[75] Inventors: Daniel A. Talonn, University City; Alan B. Ranford, St. Louis, both of Mo.

[73] Assignee: Sherwood Medical Company, St. Louis, Mo.

[21] Appl. No.: 717,592

[22] Filed: Jun. 19, 1991

Related U.S. Application Data

[62] Division of Ser. No. 212,528, Jun. 28, 1988, Pat. No. 5,053,018.

[51] Int. Cl.$^5$ ............................................. A61M 5/32
[52] U.S. Cl. ................................. 604/198; 604/110; 128/763; 128/919
[58] Field of Search ................. 609/194–198, 609/192, 263, 110; 128/919, 763, 770

[56] References Cited

U.S. PATENT DOCUMENTS

| | | |
|---|---|---|
| 2,571,653 | 10/1951 | Bastien . |
| 3,780,734 | 12/1973 | Wulff . |
| 3,890,971 | 6/1975 | Leeson et al. . |
| 4,139,009 | 2/1979 | Alvarez . |
| 4,356,822 | 11/1982 | Winstead-Hall . |
| 4,425,120 | 1/1984 | Sampson et al. ............... 604/198 |
| 4,573,976 | 3/1986 | Sampson et al. ............... 604/198 |
| 4,631,057 | 12/1986 | Mitchell ............... 604/198 |
| 4,643,199 | 2/1987 | Jennings, Jr. et al. ............... 128/763 |
| 4,650,468 | 3/1987 | Jennings, Jr. ............... 604/110 |
| 4,655,751 | 4/1987 | Harbaugh ............... 604/198 |
| 4,666,435 | 5/1987 | Braginetz ............... 604/198 |
| 4,681,567 | 7/1987 | Masters et al. ............... 604/198 |
| 4,693,708 | 9/1987 | Wanderer et al. ............... 604/198 |
| 4,695,274 | 9/1987 | Fox ............... 604/198 |
| 4,702,738 | 10/1987 | Spencer ............... 604/198 |
| 4,723,943 | 2/1988 | Spencer ............... 604/198 |
| 4,731,059 | 3/1988 | Wanderer et al. ............... 604/192 |
| 4,737,144 | 4/1988 | Choksi ............... 604/198 |
| 4,743,233 | 5/1988 | Schneider ............... 604/192 |
| 4,758,231 | 7/1988 | Haber et al. ............... 604/198 |
| 4,772,272 | 9/1988 | McFarland ............... 604/198 |
| 4,782,841 | 11/1988 | Lopez ............... 128/164 |
| 4,790,828 | 12/1988 | Dombrowski et al. ............... 604/198 |
| 4,801,295 | 1/1989 | Spencer ............... 604/198 |
| 4,810,248 | 3/1989 | Masters et al. ............... 604/192 |
| 4,813,426 | 3/1989 | Haber et al. ............... 128/763 |
| 4,842,587 | 6/1989 | Poncy ............... 604/198 |
| 4,846,796 | 7/1989 | Carrell et al. ............... 604/110 |
| 4,871,355 | 10/1989 | Kikkawa ............... 604/198 |
| 4,874,383 | 10/1989 | McNaughton ............... 604/198 |
| 4,923,445 | 5/1990 | Ryan ............... 604/195 |
| 4,927,018 | 5/1990 | Yang et al. ............... 206/365 |
| 4,929,237 | 5/1990 | Medway ............... 604/198 |
| 4,935,016 | 6/1990 | Deleo ............... 604/198 |
| 4,976,702 | 12/1990 | Andrews et al. ............... 604/198 |
| 4,994,045 | 2/1991 | Ranford ............... 604/198 |
| 4,998,920 | 3/1991 | Johnson ............... 604/198 |
| 4,998,924 | 3/1991 | Ranford ............... 604/198 |
| 5,011,479 | 4/1991 | Le et al. ............... 604/198 |
| 5,019,051 | 5/1991 | Hake ............... 604/198 |
| 5,024,616 | 1/1991 | Ogle ............... 604/192 |
| 5,024,660 | 6/1991 | McNaughton ............... 604/110 |
| 5,030,209 | 7/1991 | Wanderer et al. ............... 604/198 |
| 5,045,066 | 9/1991 | Scheuble et al. ............... 604/198 |
| 5,053,018 | 10/1991 | Talonn et al. ............... 604/198 |
| 5,059,185 | 1/1991 | Ryan ............... 604/198 |
| 5,088,988 | 2/1992 | Talonn et al. ............... 604/198 |

*Primary Examiner*—C. Fred Rosenbaum
*Assistant Examiner*—Mark O. Polutta
*Attorney, Agent, or Firm*—Andrew J. Beck; Montgomery W. Smith; Richard D. Allison

[57] ABSTRACT

A safety device including a protective needle shield which is movable between a retracted position wherein a needle is exposed and an extended position wherein the needle is protected. The needle shield including an inwardly directed and longitudinally oriented key member thereon and an elongate barrel member includes a collar member operatively associated therewith such that the key member is movably received in a keyway on the collar member as the needle shield is moved between the retracted and extended positions. The collar member also includes a locking slot thereon to receive a portion of the key member as the needle shield is rotated about the barrel member in the extended position of the needle shield.

24 Claims, 3 Drawing Sheets

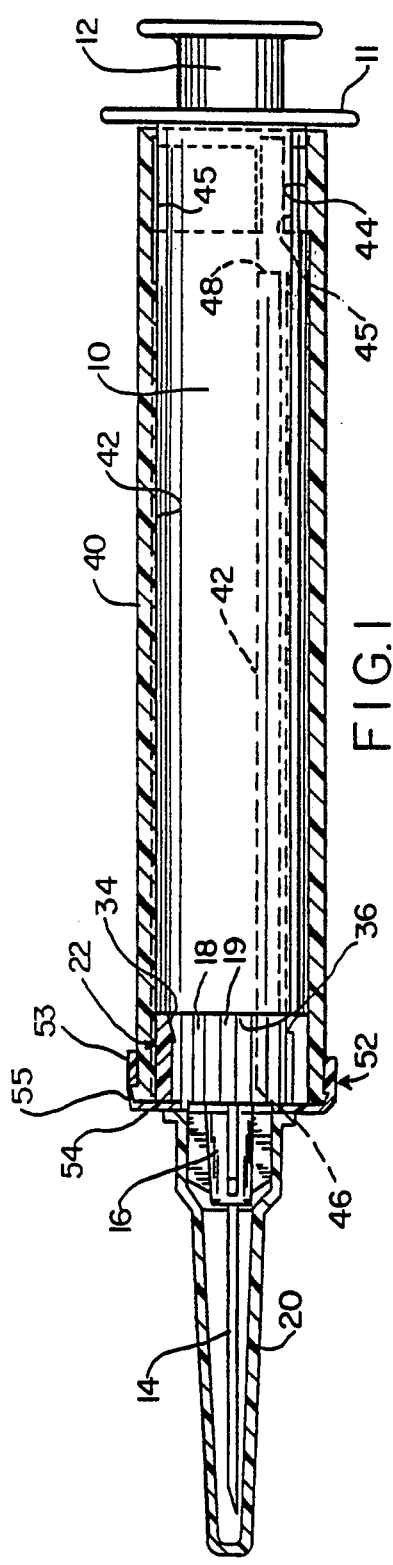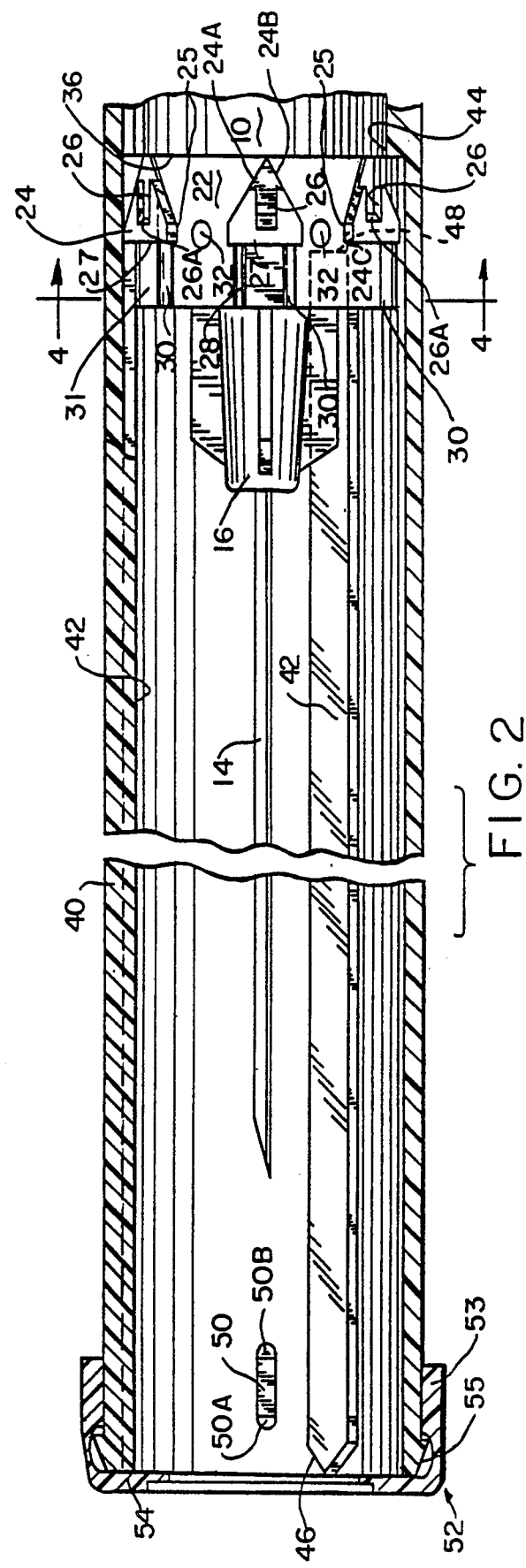

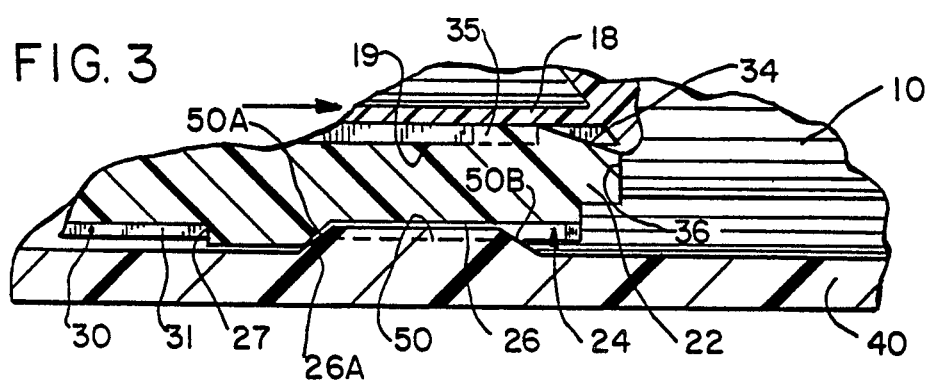
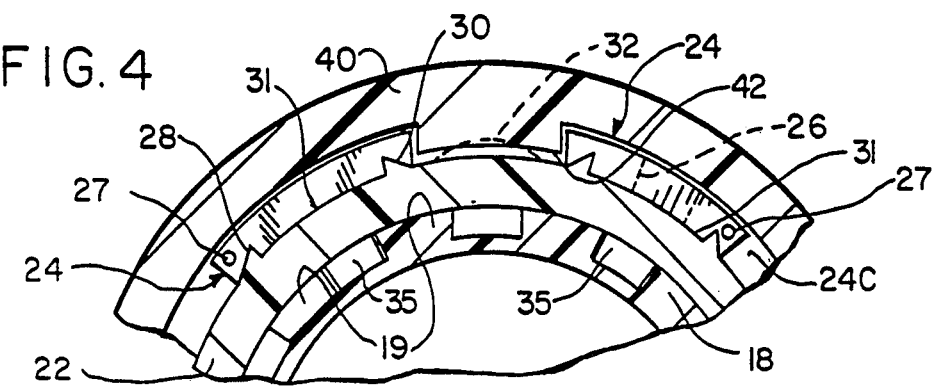
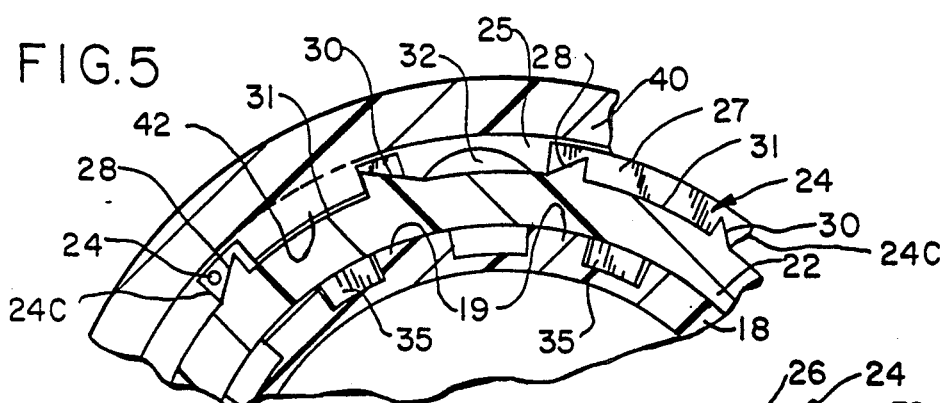
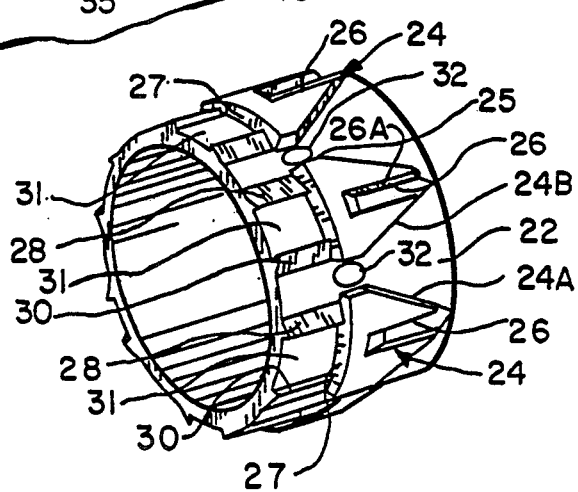

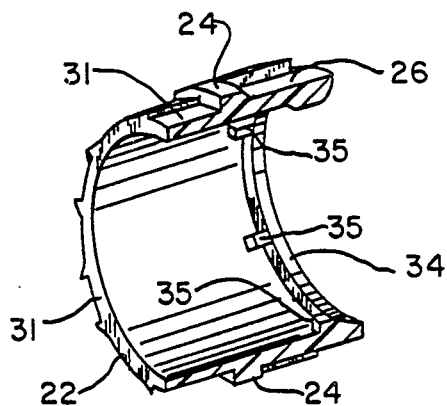
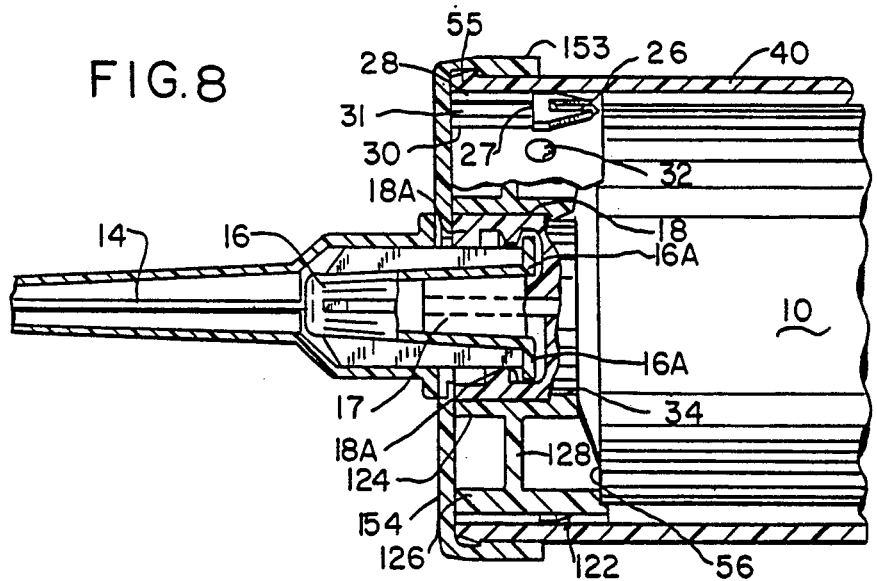
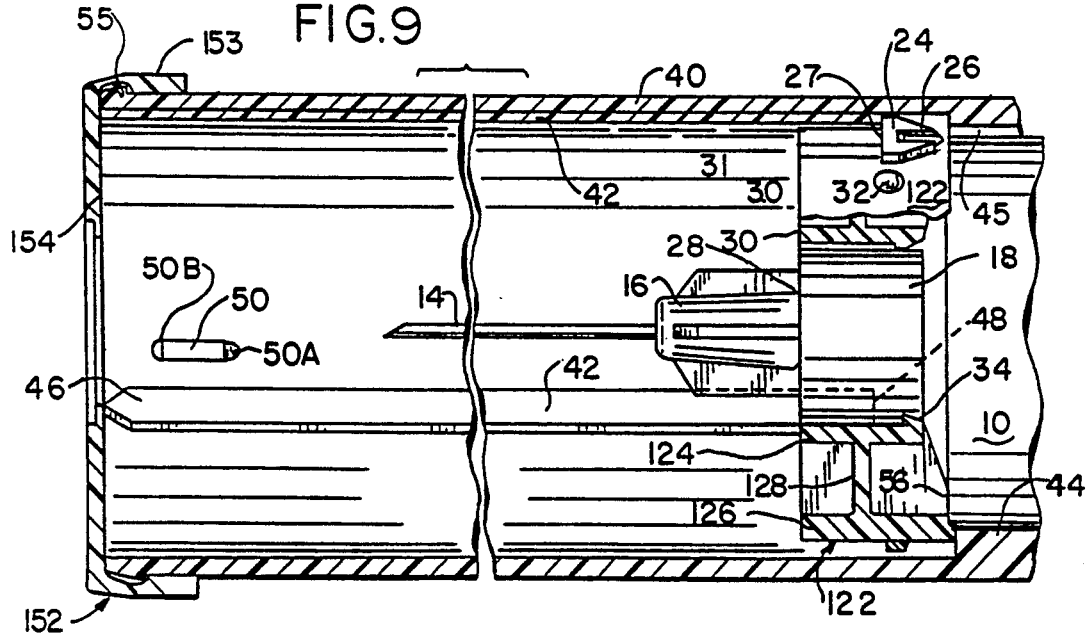

COMBINED SYRINGE AND NEEDLE SHIELD

This is a divisional of copending application Ser. No. 07/212,528, filed on Jun. 28, 1988, now U.S. Pat. No. 5,053,018.

This invention relates to syringes and, in particular, to a hypodermic syringe having a retractable needle guard primarily for the purpose of preventing accidental needle sticks.

Most syringes used today for medical or laboratory purposes are sold as disposable items intended to be used only once. Disposal of such syringes has posed a safety hazard for the individuals who use the syringes as well as for those who dispose of them. With the onset of AIDS, the concern for infection due to accidental needle sticks from used syringes has increased and a number of different devices have been proposed to minimize the possibility of spreading infectious disease due to accidents of this type.

One approach to this problem is to provide a retractable shield which, after the syringe has been used, can be pulled to an extended position where it covers the needle, making it difficult for an individual to accidentally contact the needle. A common feature of such constructions is that when the shield is pulled to its extended position, it is locked so that it cannot be retracted (thus exposing the needle) except by application of extraordinary force.

A number of such constructions have been proposed to satisfy the general requirement that the needle be permanently covered after the syringe has been used. Some of these constructions involve twist-to-lock mechanisms and, in others, locking occurs automatically when the shield is fully extended. These known devices satisfy many of the functional requirements of a needle shield but require, in most cases, modification of the standard syringe construction. This is highly undesirable for some manufacturers because of the sizable investment they may have already made in their existing molding equipment for producing the syringes.

Moreover, certain operational problems arise when a shield is incorporated into a syringe. For example, since the shield, when it is retracted, essentially covers the barrel of the syringe, it is desirable to be able to insert and remove a needle while holding onto the shield alone. This involves twisting and pushing (or pulling) the needle to place it on (or remove it from) the luer and can be awkward with some known constructions.

Further, constructions have been proposed which include an opening or slot in the side of the shield. This is undesirable because the needle can extend through the opening if the shield is deflected in the extended position.

Those devices which lock in response to axial movement to the extended position, (i.e., without any rotation) have certain inherent drawbacks that result primarily from the requirement that substantial force be exerted axially to lock the shield in its extended position. In the first place, the likelihood of unintentional and irreversible locking is greater with such devices than with those devices which require rotation to lock. Also, it is difficult to verify that the shield is locked upon such forcible extension without attempting to retract the shield, which increases the possibility of unintended exposure of the needle. Finally, if the user's hand should slip from the shield while exerting the force necessary to extend the shield to the locked position, the user's hand may reflexively rebound back onto the needle point if the shield does not actually lock.

Other proposed devices have included open ended shields which would not block access to the needle point by small fingers.

Accordingly, it is an object of this invention to provide a protective shield of the type described which can be added at minimal expense to standard syringes.

Another object of the invention is to provide a relatively inexpensive protective shield which satisfies the functional requirements of a needle shield and includes none of the drawbacks mentioned above.

Another object is to provide an extendable needle shield for a syringe which performs all of the necessary functions of such a shield and which is particularly well suited to an automated process of manufacture.

A further object of the invention is to provide an extendable needle shield for a standard syringe which is improved both from the points of view of functional utility and cost of manufacture.

A still further object is to provide an inexpensive method of assembling a protective shield and syringe.

SUMMARY OF THE INVENTION

In accordance with the invention, a needle shield is mounted coaxially on a syringe barrel. The shield includes one or more elongated keys on its inner surface. A collar is provided on the forward end of the barrel. The collar may be a separate part or it may be integrally formed with the barrel and includes on its outer surface at least one locking slot. The key slides in a path outside of the locking slot and can be rotated into the locking slot when the shield is extended. Both the collar and shield can be molded from plastic materials so that the cost of the shield is relatively low.

In a preferred embodiment, the shield includes a plurality of elongated locking keys and the collar includes a plurality of locking slots. Each locking slot is defined by opposing walls, at least one of which includes a ramp over which the keys can ride when the shield is pulled to its extended position and rotated.

In the preferred embodiment, when the keys are rotated into the locking slots, rearward movement of the shield to its retracted position is prevented by a surface on the collar at the back of each locking slot. In accordance with a further feature of the invention, protrusions on the collar and the forward portions of the keys are shaped such that during assembly the keys are directed into keyways formed between the locking slots as the collar is moved relative to the shield. Thus, the construction is well suited to an automated process in which the collar and shield are secured to the syringe by machine.

Other benefits of the invention are set forth below in the detailed description which follows:

IN THE DRAWINGS

FIG. 1 is a side elevational view, partly in section, showing a needle shield and collar in accordance with a preferred embodiment of the invention secured to a conventional syringe with the shield in its retracted position;

FIG. 2 is an enlarged sectional view with the shield in cross-section in its extended position;

FIG. 3 is a further enlarged partial side sectional view showing details of the collar and shield;

FIG. 4 is a sectional view along the line 4—4 of FIG. 2 with the shield pulled to its extended position but before rotation;

FIG. 5 is a sectional view along the line 4—4 of FIG. 2 showing the shield rotated into its locked position;

FIG. 6 and 7 are perspective views of a preferred embodiment of the collar;

FIG. 8 is a side sectional view showing a collar construction for use with a large diameter barrel; and FIG. 9 is an enlarged side sectional view showing a shield in its extended position relative to the collar of FIG. 8.

DETAILED DESCRIPTION

In its preferred embodiment, the invention is intended to be used in conjunction with a conventional syringe; however, a protective shield in accordance with the invention can be used for any medical or laboratory device having a needle, such as a blood collection tube holder with a double ended needle. Accordingly, as used herein, the term "syringe" is intended to include any medical or scientific device including a needle wherein it is desired to protect a user from accidental needle sticks.

In describing the invention, the "distal end" of a part refers to the end of the part closest to the needle point. The "proximal end" of a part refers to the end furthest from the needle point.

FIGS. 1–6 show a conventional syringe comprising a tubular barrel 10 having a finger flange 11, a plunger 12 slidable within the barrel 10, and a needle assembly through which the contents of the barrel are dispensed when the plunger 12 is depressed. The barrel 10 may be tapered very slightly (not shown) from a larger diameter proximal end to a smaller diameter distal end for molding purposes. The needle assembly comprises a needle 14 and a hub 16 at the proximal end of the needle. As is standard, a conically shaped luer tip 17 and luer lock skirt 18 are integrally formed at the distal end of barrel 10 with luer lock skirt 18 encircling luer tip 17. As shown in FIG. 8 (directed to a different collar construction and described in detail below), the interior surface of the luer lock skirt 18 includes an internal thread 18A adapted to threadably engage complementary locking ears 16A on the needle hub 16. The exterior surface of luer lock skirt 18 includes a multiplicity of ribs 19 parallel to the central axis of the barrel. The needle and luer arrangement of FIG. 8 is the same as that of FIGS. 1–6.

A needle sheath 20 covers needle 14 as a protective device. Sheath 20 frictionally engages hub 16 and can be used to disconnect the needle assembly from the luer lock skirt 18 in conventional fashion.

The construction as so far described is that of a standard disposable syringe and forms no part of the invention.

The collar employed in accordance with the preferred embodiment of the invention is shown generally at 22 (FIGS. 2, 6 and 8). As mentioned above, although collar 22 is shown as a separate piece, the collar (or its functional equivalent) may be integrally formed as a part of the barrel 10. It includes six equally spaced and integrally formed identical triangular protrusions 24, with the apex of each protrusion extending away from the needle. Keyways 25 are formed between each adjacent pair of protrusions 24.

The triangular protrusions 24 each include angled surfaces 24A and 24B, side surfaces 25C, a slot 26 and a surface 27 which is generally circumferential and functions as a stop as explained below. The slot 26 includes a sloped distal surface 26A. It is not necessary that protrusions 24 be triangular in shape and other configurations can be used to provide a stop 27 for the keys and the angled surfaces 25A and 25B necessary to guide the keys into the keyways during the assembly process as described below. The slot 26 is formed in protrusion 24 and extends proximally to the point of the protrusion 24 to expose the detenting surface 26A and facilitate the entry of the detent 50 into the slot 26 during assembly, and also to facilitate efficient molding of the collar. At the forward end of each protrusion, two walls 28 and 30 extend toward the needle. A rectangular locking slot 31 is formed between each pair of walls 28 and 30, which are ramp shaped in cross section as shown most clearly in FIGS. 4, 5 and 6. As shown in FIGS. 3, 4, 5 and 6, the surface of locking slot 31 is slightly elevated relative to the level of the keyways 25, i.e., the barrel diameter at the locking slots 31 is slightly greater than the barrel diameter at the keyways. The slight increase in the collar diameter at the locking slots removes some of the slack between the needle shield (described below) and the collar 22 resulting from the slight taper of the barrel 10 in the preferred embodiment. This prevents or at least minimizes wobble or play of the shield when it is locked in the extended position. A circular detent 32 is positioned between each pair of triangular protrusions 24 with the forward points of detents 32 lying just in front of the bases of triangular projections 24.

As shown most clearly in FIG. 3, the rear end of collar 22 includes a peripheral rigid tooth 34 adapted to engage the ribs 19 in the luer lock skirt 18 to retain the collar 22 on the syringe. Collar 22 is molded of a rigid plastic material such as polycarbonate resin so that when the collar is pushed over the luer lock skirt 18, the angled surface of the rigid tooth 34 allows the tooth to move over the ribs 19 until the proximal end of the collar is seated toward the distal end of the barrel with the rigid tooth 34 deforming the ribs 19 of the luer lock skirt 18 to permanently retain the collar in place on the syringe barrel 10. As an alternative, a circumferential groove may be formed in collar 22 to receive the peripheral tooth 34. This is unnecessary in the preferred embodiment in which the yieldable ribs 19 cold flow into the configuration shown in FIG. 3 but may be desirable in the case of syringes which do not include ribs molded on the exterior surface of the luer lock skirt. Instead of mechanically interlocking the collar 22 and barrel 10, other fastening means such as sonic welding or adhesives may be used within the scope of the invention, although such techniques are generally disadvantageous because of the additional steps involved and other problems which may arise with the preferred assembly techniques. The diameter of collar 22 as measured in the area of the keyways 25 is greater than the outer diameter of the syringe barrel 10 adjacent the collar.

Locking lip 34 will bite sufficiently into the outer surface of the luer skirt 18 to prevent axial movement of collar 22 but in some cases slight rotation or rocking of the collar may occur. To prevent this, the tooth 34 may be formed with gaps (not shown) so that not all of the ribs 19 on the outside of the luer lock skirt 18 will be deformed. The nondeformed ribs 19 falling into the gaps resist rotation or rocking of the collar 22 relative to barrel 10. Alternatively, as shown in FIGS. 3 and 7, the inner surface of collar 22 may be provided with lugs 35 molded on the inside of the collar and adapted to fit between the ribs 19 on the outside of the luer lock skirt 18 to prevent positively any rotational movement with the meshed ribs 19.

The needle shield comprises an elongated plastic cylinder 40 (e.g., made of polypropylene) having three keys 42 integrally formed on its interior surface. An end rim 44 is formed at the proximal end of shield 40. As shown in FIG. 2, end rim 44 is adapted to abut against the proximal end of collar 22 to limit the forward movement of the shield. Each of the keys 42 includes a distal triangular point 46 and extends from the distal end of the shield to a point just short of the distal point of the triangular protrusions 24 on collar 22 when the shield is in its extended position as shown in FIG. 2. End rim 44 includes three cutout sections 45 which align with each of the keys 42. Cutout sections 45 facilitate the process for molding keys 42 but serve no functional purpose after the device has been assembled. At their rear ends, the keys 42 terminate in flat surfaces 48. With the three keys 42 in the keyways 25 in the retracted position (FIG. 1), rotational movement of the shield 40 is prevented by abutment of the edges of keys 42 against the side surfaces 24C of protrusions 24; therefore, torque can be applied to the needle while holding shield 40 to thread (or unthread) needles onto (or from) the syringe. This cannot be done with constructions in which a shield rotates freely with respect to the syringe.

Three detents 50 are also formed on the inner surface of the shield 40 toward its forward end. The detents 50 may be equally spaced and are adapted to be received within the slots 26 in the triangular protrusions 24 to retain the shield 40 in its retracted position (FIG. 1). In the preferred embodiment, as shown in the drawings, the detents 50 are each spaced thirty degrees from an adjacent key 42. It is not necessary that the detents be equally spaced. Each of the detents includes a sloped distal surface 50A and a proximal surface 50B more gradually sloped than slope 50A.

In the retracted position, the distal end of shield 40 terminates at the same point as the distal end of collar 22. An end cap 52 (see FIG. 2) is placed on the forward end of the shield 40. Cap 52 is molded from a resilient plastic material (such as polyallomer) and includes a side wall 53 and an end wall 54 which is adapted to be positioned between the distal end of collar 22 and the proximal end of the needle sheath 20 (FIG. 1) for substantially closing the distal end of shield 40. Side wall 53 is shaped as shown so that end cap 52 can be retained on shield 40 by the interlocking mechanical engagement of the side wall 53 and a complementary projection 55 at the forward end of shield 40. Cap 52 need not be a separate part and can, instead, be formed as an integral part of shield 40.

The end wall 54 includes a central needle aperture which is made small enough that the end of shield 40 is closed to the maximum extent while allowing the locking ears 16A of needle hub 16 to be extended through the aperture to permit needles to be mounted and removed while the shield 40 is in its retracted position (FIG. 8). The aperture is not, however, large enough to allow the proximal end of the sheath to pass through it. The minimum needle aperture reduces the likelihood that a child or person with small fingers may accidentally contact the needle point. End cap 52 also makes the distal end of shield 40 more rigid and resistive to deformation when dropped or otherwise impacted upon a hard surface.

In addition, the rim 54 and its position between the proximal end of needle sheath 20 and the distal end of barrel 10 serves a functional purpose when removing or installing needles on the luer tip 17 (FIG. 8), for example, when the filling and injection needles are different. When a needle is to be mounted on a syringe, the syringe is held by shield 40 with the shield in its retracted position. Needle hub 16, projecting from the proximal end of the protective sheath 20, is inserted through the aperture in the end wall 54 and the hub telescoped onto the luer tip 17. Using the conventional cooperative wrenching tabs (not numbered) of the sheath and needle, the needle hub 16 is rotated by twisting and pushing with the sheath to thread the locking tabs 16A within the internal threads 18A in the luer skirt 18 until needle 14 is mounted on the syringe. As hub 16 is threaded onto the luer tip 17, the needles move axially relative to sheath 20. The shield 40 is prevented from rotating by abutment of keys 42 against surfaces 24C of protrusions 26, while the rim 54 provides a surface against which the needle sheath can be forced. Without this feature, the user could not grasp the shield alone when installing and removing the needle since the force exerted by the needle hub on the syringe luer tip would push the syringe out of the shield. This would mean that the user would have to remember to grasp the barrel and not the shield when removing and attaching the needle.

The end wall 54 is particularly important when the invention is used in conjunction with large diameter barrels. Such a construction is shown in FIGS. 8 and 9 wherein like numerals are used to identify parts identical to those shown in the embodiment of FIGS. 1–6. In FIGS. 8 and 9 the needle 14 and hub 16 are the same as in FIG. 1 as is the luer tip 17 and the luer lock skirt 18. In this case, however, the collar 122 includes two concentric hubs or sleeves 124 and 126 supported by an annular strut 128 preferably forming an I-beam in cross-section as shown in FIG. 9. The cross-sectional shape is not critical, however, and those skilled in the art will readily understand that the cross-section could be cup- or channel-shaped, with a web extending either distally or proximally between the concentric hubs or sleeves. The end cap 152 includes side wall 153 and end wall 154 which, as shown, covers a substantial portion of the barrel opening and thus greatly reduces the risk of accidental needle stick when the shield is in its extended position.

The device may be assembled as follows. Shield 40 is inserted on the forward end of the barrel 10 of an assembled syringe to its retracted position shown in FIG. 1 (prior to installation of the needle 14 and sheath 20 on the syringe). With the shield 40 held in position, the collar 22 is then placed over the luer lock skirt 18 inside of the shield 40. Engagement of the triangular protrusions 24 on collar 22 with the triangular points 46 at the end of keys 42 on shield 40, as the collar 22 is pushed onto the luer lock skirt 18, causes the shield 40 to rotate until the keys 42 are positioned in the keyways over detents 32 between adjacent triangular protrusions 24. The collar 22 is pushed inwardly until the proximal end of the collar butts up against the face 56 on the syringe barrel 10. In this position, as shown in FIG. 3, the three detents 50 are seated in the slots 26 of three of the protrusions 24. After the shield 40 and collar 22 have been assembled on the syringe, end cap 52 is placed on the shield 40. The needle 14 with its sheath 20 may then be attached to the luer tip to complete the assembly.

Alternatively, collar 22 may be positioned within shield 40 with the keys 42 positioned in the appropriate keyways 25. The shield and collar may then be telescoped together over the syringe barrel with the collar being forced onto the luer lock skirt as the shield is moved to the retracted position in which the proximal end of the collar abuts against the distal face of the syringe barrel. This procedure, with appropriate tooling, may be used with the end cap 52 in place on the shield which means that this assembly process could be used with a shield having end wall 54 integrally formed as a portion of the shield as mentioned above. Conversely, this alternative assembly method can be used with an open shield in which case end cap 52 can be placed on the shield after assembly.

The use of the syringe may be conventional. Needle sheath 20 is removed and medication drawn into barrel 10 by withdrawal of plunger 12 with the shield in its retracted position shown in FIG. 1. After the contents of the syringe have been injected into a patient, the shield 40 is pulled forward into the extended position shown in FIG. 2. When this happens, the keys 42 slide in the keyways 25 over detents 32 between the adjacent protrusions 24 on collar 22 (FIG. 4) and the distal surfaces 50A of detents 50 slide over surfaces 26A (FIG. 2) of slots 26. The user can feel the rear edges 48 of keys 42 clearing detents 32, which signals that the shield 40 is fully extended.

To lock the shield in place, the user rotates shield 40 causing the keys 42 to move over the adjacent ramps 28 (or 30) until the keys fall into the locking slots 31 formed between each pair of ramps 28 and 30 (see FIG. 5). Because of the arrangement of the ramps 28 and 30, the shield can be locked by rotating it either clockwise or counterclockwise. When the keys 42 are positioned in the locking slots 31, the rear edge 48 of each key abuts against the squared off surface 27 of one of the triangular protrusions 24 so that the shield cannot be returned to its retracted position without application of excessive force. Because of the interlocking relationship of the square key and locking slots, shield 40 can no longer be rotated and, accordingly, the shield is permanently locked in place.

There are circumstances where it may be desirable to extend the shield 40 to the position shown in FIG. 2 without locking it in place. For example, if a syringe is to be filled at a location remote from the patient, rather than replacing the sheath 20 after the syringe is filled, it is preferable to extend shield 40 so that it functions as a temporary protective element while the syringe is carried to the patient. Use of the protective shield 40 in this fashion is facilitated by the detents 32 on collar 22. These detents 32 are positioned in each of the keyways 25 between the triangular protrusions 24 so that when the shield 40 is pulled to its extended position (FIG. 2), the flat end 48 of each of the keys 42 abut against one of the detents 32. This prevents the shield 40, when it is in its extended position, from being retracted unless sufficient force is applied to move the keys 42 over the detents 32. Hence, in this situation, the shield is first extended as a temporary sheath for the needle, returned to its retracted position for the patient's injection, and then finally again extended and locked by rotation so that the shield cannot be retracted. If it is desired to return the shield 40 to its retracted position rather than locking the shield in its extended position, because of the gradual slope of surface 50B of detent 50, the detent can be pushed over the squared off surface 27.

What is claimed is:

1. A needle shielding device for use with a barrel, wherein a needle may be attached to the distal end of the barrel, the improvement comprising:
    shield retaining means mounted on said barrel in use and including at least one locking slot and a keyway on an outer surface thereon and said keyway being longitudinally oriented therealong and includes distal and proximal ends thereon, and
    an elongated needle shield having an inner surface and being movable over said barrel and retaining means between a retracted position in which the needle is exposed and an extended position in which the needle is exposed and an extended position in which said shield covers said needle, said shield including at least one elongated key extending inwardly on its interior surface, said key adapted to slide through said keyway between said retracted and extended positions and wherein said key is an elongate and longitudinally oriented member extending inwardly from said inner surface of said shield and includes distal and proximal ends thereon.

2. The needle shielding device according to claim 1, wherein said locking slot comprises a pair of opposing walls at least one of which includes a ramp surface over which said key can ride when said shield is rotated about said barrel, and a protrusion proximally of said locking slot for preventing said shield from being retracted after said key has been rotated into said locking slot.

3. The needle shielding device according to claim 2, wherein each of said opposing walls includes a ramp surface so that said key can be rotated in either direction into said locking slot when said shield is in said extended position.

4. The needle shielding device according to claim 1, wherein said shield includes a detent on said interior surface and said shield retaining means includes a surface adapted to abut against said detent to releasably retain said shield in said retracted position.

5. The needle shielding device according to claim 1, wherein said shield retaining means includes at least one detent on said outer surface adapted to abut against said proximal end of said key when said shield is in said extended position.

6. The needle shielding device according to claim 1, wherein said needle incudes a hub at a proximal end thereof and a protective needle sheath having a proximal end thereon and wherein said shield includes an end wall at the distal end thereof, said end wall including an aperture large enough to permit said hub of said needle to pass therethrough for mounting and removing said needle on said barrel but not large enough to permit said proximal end of said sheath to pass therethrough.

7. The needle shielding device according to claim 1, wherein said shield includes an inwardly extending rim adapted to abut against the proximal end of said shield retaining means to limit the forward movement of the shield beyond said extended position.

8. A needle shielding device for use with a barrel, wherein a needle may be attached to the distal end of the barrel, the improvement comprising:
    shield retaining means operatively mounted on said barrel and including at least one locking slot and a keyway on an outer surface thereon and said keyway being longitudinally oriented therealong and includes distal and proximal ends thereon, and an elongated needle shield having an inner surface and being movable over said barrel and retaining means between a retracted position in which the needle is exposed and an extended position in which the needle is exposed and an extended position in which said shield covers said needle, said shield including at least one elongated key extending inwardly on its interior surface, said key adapted to slide through said keyway between said retracted and extended positions and wherein said key is an elongate and longitudinally oriented member extending inwardly from said inner surface of said shield and includes distal and proximal ends thereon; and wherein the distance between said distal and proximal ends of said key on said shield is greater than the distance between said distal and proximal ends of said keyway on said shield retaining means.

9. The needle shielding device according to claim 8, wherein said keyway is formed by projections extending radially outwardly from the exterior surface of said shield retaining means.

10. The needle shielding device according to claim 8, wherein said key and said keyway also prevent rotation of said shield about said barrel when said shield is in any position other than said extended position.

11. The needle shielding device according to claim 1, wherein said shield retaining means is a collar member separate from said barrel and wherein there is provided interlocking means on said collar member and said barrel for preventing rotation of said collar member about said barrel.

12. A needle shielding device comprising:
a barrel having a distal end and a needle operatively associated with said distal end of said barrel,
collar means mounted on said barrel in use, said collar means including at least one longitudinally oriented keyway having distal and proximal ends thereon,
an elongated needle shield having an inner surface and distal and proximal ends thereon and being movable over said barrel and collar means between a retracted position wherein said needle is exposed and an extended position wherein said needle is protected, and
at least one elongated key member oriented longitudinally along and inwardly from said inner surface of said shield and said key member including distal and proximal ends and wherein said key is slidably received through said keyway as said shield is moved between said retracted and extended positions.

13. A needle shielding device comprising:
a barrel having a distal end and a needle operatively associated with said distal end of said barrel,
collar means operatively mounted on said barrel, said collar means including at least one longitudinally oriented keyway having distal and proximal ends thereon,
an elongate needle shield having an inner surface and distal and proximal ends thereon and being movable over said barrel and collar means between a retracted position wherein said needle is exposed and an extended position wherein said needle is protected,
at least one elongated key member oriented longitudinally along and inwardly from said inner surface of said shield and said key member including distal and proximal ends and wherein said key is slidably received through said keyway as said shield is moved between said retracted and extended positions, and wherein the distance between said distal and proximal ends of said key is greater than the distance between said distal and proximal ends of said keyway.

14. The needle shielding device of claim 12 wherein said collar means includes a locking slot spaced apart from said keyway and said proximal end of said key is rotatable into said locking slot when said shield is in said extended position.

15. The needle shielding device of claim 12 wherein said shield includes a reduced diameter distal end thereon and said needle includes a proximal end thereon and a protective needle sheath removably received thereover, said distal end of said shield including an aperture therein to allow said needle to pass therethrough while preventing the passage of said needle sheath therethrough.

16. The needle shielding device of claim 12 wherein said key member slides in said keyway between said retracted and extended positions and said projections on said collar means prevent the rotation of said shield about said barrel as said shield is moved to said extended position.

17. The needle shield device of claim 12 wherein said collar means includes a locking slot spaced from said keyway on said collar means and a rotation preventing means is positioned between said keyway and said locking slot to prevent said shield from being rotated from said locking slot after said key is received in said locking slot.

18. The needle shielding device of claim 12 wherein said distal end of said shield includes a detent on said inner surface and said collar means includes a cooperating means thereon to contact said detent and releasably retain said shield in said retracted position.

19. The needle shielding device of claim 12 wherein said collar means is a cylindrical member fixedly positioned about a portion of said barrel.

20. A needle shielding device comprising:
a barrel having a distal end and a shield attached to said distal end,
collar means operatively mounted on said barrel and including at least one longitudinally oriented keyway formed by a plurality of radially outwardly extending projections thereon, said keyway including distal and proximal ends thereon,
an elongate needle shield having an inner surface and distal and proximal ends and being movable over said barrel and said collar means between a retracted position wherein said needle is exposed and an extended position wherein said needle is protected,
at least one elongated key member oriented longitudinally along and extending from said inner surface of said shield between said distal and proximal ends of said shield, said key member having distal and proximal ends thereon and adapted to be movably received in said keyway as said shield is moved between said retracted position and said extended position, and
wherein the distance between said proximal and distal ends of said collar means is less than the distance between said distal and proximal ends of said key.

21. The needle shielding device of claim 20 wherein a locking slot is radially spaced apart from said keyway and said key member is rotatable into said locking slot when said shield is in said extended position.

22. The needle shielding device of claim 21 wherein a ramp member is positioned between said keyway and said locking slot to retain said proximal end of said key member in said locking slot when said shield is rotated about said barrel.

23. The needle shielding device of claim 20 wherein said projections on said collar means prevents the rotation of said shield about said barrel until said shield reaches said extended position whereupon said proximal end of said key member is rotatable from said keyway into said locking slot.

24. The needle shielding device of claim 20 wherein said collar means is a cylindrical member fixedly attached to said distal end of said barrel and includes a locking slot formed by a plurality of ramp-shaped members is located on said collar means in a location radially spaced apart from said keyway to receive said proximal end of said key therein upon rotation of said shield in said extended position about said barrel.

* * * * *